United States Patent
Iddan et al.

(10) Patent No.: US 9,958,253 B2
(45) Date of Patent: May 1, 2018

(54) SYNCHRONIZED DUAL MODE OCT SYSTEM

(71) Applicant: COLLAGE MEDICAL IMAGING LTD., Beer-Sheva (IL)

(72) Inventors: Gavriel J. Iddan, Haifa (IL); Roni Zvuloni, Haifa (IL)

(73) Assignee: Collage Medical Imaging Ltd., Beer-Sheva (IL)

( * ) Notice: Subject to any disclaimer, the term of this patent is extended or adjusted under 35 U.S.C. 154(b) by 0 days. days.

(21) Appl. No.: 15/517,959

(22) PCT Filed: Oct. 8, 2015

(86) PCT No.: PCT/IL2015/051008
§ 371 (c)(1),
(2) Date: Apr. 9, 2017

(87) PCT Pub. No.: WO2016/056015
PCT Pub. Date: Apr. 14, 2016

(65) Prior Publication Data
US 2017/0234675 A1    Aug. 17, 2017

Related U.S. Application Data

(63) Continuation-in-part of application No. PCT/IL2015/050782, filed on Jul. 29, 2015.
(Continued)

(51) Int. Cl.
*G01B 9/02* (2006.01)
*A61B 5/00* (2006.01)
*A61B 10/04* (2006.01)

(52) U.S. Cl.
CPC ........ *G01B 9/02069* (2013.01); *A61B 5/0066* (2013.01); *A61B 5/7214* (2013.01);
(Continued)

(58) Field of Classification Search
CPC ............ G01B 9/02002; G01B 9/02004; G01B 9/02005; G01B 9/02069; G01B 9/02014; H01S 3/00
See application file for complete search history.

(56) References Cited

U.S. PATENT DOCUMENTS 5,227,648 A    7/1993    Woo
6,564,087 B1   5/2003    Pitris et al.
(Continued)

FOREIGN PATENT DOCUMENTS

CN    201542612 U    8/2010
CN    203153684 U    8/2013
WO    2013157006 A1  10/2013

OTHER PUBLICATIONS

Huang D. et al., "Optical Coherence Tomography", Science, vol. 254, No. 5035, pp. 1178-1181, Nov. 1991.
(Continued)

*Primary Examiner* — Jonathan Hansen
(74) *Attorney, Agent, or Firm* — The Roy Gross Law Firm, LLC; Roy Gross

(57) ABSTRACT

The present application in some embodiments relates to methods for reducing noise and/or clutter when measuring a spectrum, particularly but not only for OCT imaging. In some embodiments a light source is synchronized with a detector. For example a narrow band light source is synchronized with a narrow band detector. For example, the light source may scan over multiple frequency bands and/or the detector may be tuned to a frequency band synergetic to the band of the light source. For example the light source and detector may be tuned to overlapping narrow bands. Optionally the detector has a sensor set for each frequency band. Optionally some sensor sets are individually resettable. For example each set may have a reset circuit. For example, a
(Continued)

sensor set for a band not currently being measured is deactivated.

20 Claims, 10 Drawing Sheets

Related U.S. Application Data

(60) Provisional application No. 62/061,177, filed on Oct. 8, 2014, provisional application No. 62/164,610, filed on May 21, 2015, provisional application No. 62/030,131, filed on Jul. 29, 2014.

(52) U.S. Cl.
CPC ............ *A61B 5/7257* (2013.01); *A61B 10/04* (2013.01); *G01B 9/02004* (2013.01); *G01B 9/02014* (2013.01); *G01B 9/02027* (2013.01); *G01B 9/02044* (2013.01); *G01B 9/02091* (2013.01); *A61B 2562/0233* (2013.01); *G01B 2290/45* (2013.01)

(56) References Cited

U.S. PATENT DOCUMENTS

| | | | |
|---|---|---|---|
| 7,355,716 B2 | 4/2008 | de Boer et al. | |
| 7,391,520 B2 | 6/2008 | Zhou et al. | |
| 7,519,096 B2 | 4/2009 | Bouma et al. | |
| 7,554,668 B2 | 6/2009 | Zhou et al. | |
| 7,952,718 B2 | 5/2011 | Li et al. | |
| 2008/0117427 A1 | 5/2008 | Teramura et al. | |
| 2008/0152353 A1 | 6/2008 | de Boer et al. | |
| 2009/0219515 A1* | 9/2009 | Spennemann | G01B 11/0675 356/73 |
| 2010/0097614 A1 | 4/2010 | Kourogi et al. | |
| 2011/0098572 A1 | 4/2011 | Chen et al. | |
| 2013/0012794 A1 | 1/2013 | Zeng et al. | |
| 2013/0317339 A1 | 11/2013 | Waldstreicher et al. | |
| 2013/0329006 A1* | 12/2013 | Boles | H04N 1/40056 348/42 |
| 2015/0173619 A1 | 6/2015 | Zvuloni et al. | |

OTHER PUBLICATIONS

Lee B.H. et al., "Fiber based optical coherence tomography for biomedical imaging, sensing, and precision measurements", Optical Fiber Tech, pp. 729-740, 2013.
International Search Report of PCT/IL2015/051008, dated Jan. 21, 2016; dated Jan. 24, 2016, 8 pages.
Written Opinion of PCT/IL2015/051008, dated Jan. 21, 2016; dated Jan. 24, 2016, 4 pages.

* cited by examiner

SYNCHRONIZED DUAL MODE OCT SYSTEM

CROSS-REFERENCE TO RELATED APPLICATIONS

This application is a national phase of PCT Patent Application No. PCT/IL2015/051008, filed 8 Oct. 2015, which claims priority to: U.S. Provisional Patent Application No. 62/061,177 filed 8 Oct. 2014; International Patent Application No. PCT/IL2015/050782 filed 29 Jul. 2015; U.S. Provisional Patent Application No. 62/030,131 filed 29 Jul. 2014; and of U.S. Provisional Patent Application No. 62/164,610 filed 21 May 2015, the contents of all these applications are incorporated herein by reference in their entirety.

FIELD AND BACKGROUND OF THE INVENTION

The present invention, in some embodiments thereof, relates to an adjustable frequency band optical detector and, more particularly, but not exclusively, to a system for high resolution optical coherence tomography (OCT).

U.S. Pat. No. 7,391,520 discloses, "An alternative Fourier domain optical coherence system (FD-OCT) and its associated method. The system comprises a swept multi-wavelength laser, an optical interferometer and a multi-channel receiver. By employing a multi-wavelength laser, the sweeping range for each lasing wavelength is substantially reduced as compared to a pure swept single wavelength laser that needs to cover the same overall spectral range. The overall spectral interferogram is divided over the individual channels of the multi-channel receiver and can be re-constructed through processing of the data from each channel detector. In addition to a substantial increase in the speed of each axial scan, the cost of invented FD-OCT system can also be substantially less than that of a pure swept source OCT or a pure spectral domain OCT system."

Chinese Utility Model No. 201542612 discloses, "A spectral domain OCT strobe light and sound spectra rapid detection system, including broadband light source (8), the optical isolator (10), a broadband fiber coupler (11), four polarization controller (9), the sample arm (20), the reference arm (21) and the probe arm (22); from the broadband light source (8) out of the low-coherence light passes through the first polarization controller (9), an optical isolator (10) is incident to a broadband fiber optic coupler (11), after splitting the way through the second polarization controller (9) into the sample arm (20), another pass third polarization controller (9) into the reference arm (21), the return of the light in the broadband fiber coupler After (11) in the interferometer, through the fourth polarization controller (9), into the detection arm (22); characterized in that said detection arm (22): includes a fiber collimator (1), the grating (2), the focus lens (3), radio frequency drives (4), acousto-optic modulator (5), a focusing lens (6) and the detector unit (7); into the detection arm (22) of the light from the fiber collimator (1) collimator After parallel rasterized (2) spectroscopic grating (2) and acousto-optic modulator (5) are located at a focusing lens (3) in the front focal plane and the focal plane, the light through the grating (2) after the focusing lens by spectroscopic (3) after each color light is focused on acoustic-optical modulator (5), parallel to the colored light focusing lens (3) is obliquely incident on the main optical axis acoustic-optical modulator (5), the RF drive (4) of the RF pulse signal acousto-optic modulator driver (5), the light through the narrow spectrum signal RF pulse signal drives acousto-optic modulator (5) diffraction gating time series, the focusing lens (6) Focus detection in cell detector (7), acoustic-optical modulator (5) and the detector unit (7) are placed in the focusing lens (6) and the front focal plane of the rear focal plane."

U.S. Patent Publication no. 2015/0173619 to the present inventor discloses, "Systems and methods for scanning an organ or other extended volumes of body tissue using one or more Optical Coherence Tomography (OCT) probes . . . . Some embodiments provide equipment for managing a plurality of OCT penetrations into a tissue or organ, and provide some or all of the following: detection and/or control of OCT probe positions and orientations (and optionally, that of other imaging modalities) detecting changes in body tissue positions, registering and mapping OCT scan results and optionally input from other imaging modalities, integrating OCT scan information and/or information from other modalities and/or recorded historical information, optionally some or all of the above with reference to a common coordinate system. Some embodiments comprise a display for displaying some or all of this information. In some embodiments, inferences based on observed portions of the organ relative to non-observed portions of an organ are displayed."

U.S. Pat. No. 7,554,668 discloses, " . . . a tunable semiconductor laser for swept source optical coherence tomography, comprising a semiconductor substrate; a waveguide on top of said substrate with multiple sections of different band gap engineered multiple quantum wells (MQWs); a multiple of distributed feedback (DFB) gratings corresponding to each band gap engineered MWQs, each DFB having a different Bragg grating period; and anti-reflection (AR) coating deposited on at least the laser emission facet of the laser to suppress the resonance of Fabry-Perot cavity modes. Each DFB MQWs section can be activated and tuned to lase across a fraction of the overall bandwidth as is achievable for a single DFB laser and all sections can be sequentially activated and tuned so as to collectively cover a broad bandwidth, or simultaneously activated and tuned to enable a tunable multi-wavelength laser. The laser hence can emit either a single lasing wavelength or a multiple of lasing wavelengths and is very suitable for swept-source OCT applications."

U.S. Patent Publication no. 2010/0097614 discloses, " . . . a wavelength scanning laser light source (10) provided with two Fabry-Perot resonators (13A, 13B) provided in a light path for laser oscillation. The values of FSR (free spectral range) of the Fabry-Perot resonators are set so as to be proximate to each other. The resonator length of at least one of the two Fabry-Perot resonators is periodically varied within a preset range to cause the two Fabry-Perot resonators (13A, 13B) to operate as a wavelength length varying filter of a narrow pass band capable of varying the selection wavelength by the vernier effect to output laser light that has wavelength temporally scanned. The optical coherence tomography device also includes an interference optical system (20) that causes the laser light output from the wavelength scanning laser light source (10) to be branched into light for reference and light for observation to be illuminated on an object for observation (60) and that generates interference light of reflected light of the light for observation illuminated on the object for observation (60) and the light for reference. The optical coherence tomography device further includes a signal processing means (50) that receives the interference light obtained from the interference optical system (20) for transforming the received interference light into an electrical signal to calculate the optical tomographic image information of the object for observation (60)."

U.S. Pat. No. 7,519,096 discloses, "An apparatus and source arrangement for filtering an electromagnetic radiation . . . which may include at least one spectral separating arrangement configured to physically separate one or more components of the electromagnetic radiation based on a frequency of the electromagnetic radiation. The apparatus and source arrangement may also have at least one continuously rotating optical arrangement which is configured to receive at least one signal that is associated with the one or more components. Further, the apparatus and source arrangement can include at least one beam selecting arrangement configured to receive the signal."

Additional background art includes U.S. Patent Publication no. 2015/0173619, U.S. Pat. No. 7,952,718, U.S. Pat. No. 7,952,718, and U.S. Pat. No. 6,564,087.

SUMMARY OF THE INVENTION

According to an aspect of some embodiments of the invention, there is provided a system of increased depth sensitivity OCT measurement comprising: an adjustable frequency narrow band light source; a beam splitter for dividing light from the light source along a sample and a reference path; an adjustable frequency narrow band detector positioned to receive light from both the sample and the reference paths; a controller configured for controlling a frequency and bandwidth of the light source to emit light pulses over time in a succession of narrow frequency bands, synchronizing the detector to the light source by tuning the detector to be sensitive to a respective narrow reception band that overlaps each narrow band of the succession of narrow bands when the each narrow band reaches the detector, and analyzing the output from the detector to estimate a reflectance distribution along a depth profile of the sample.

According to some embodiments of the invention, the adjustable frequency narrow band light source includes a vertical-cavity surface-emitting laser (VCSEL).

According to some embodiments of the invention, the adjustable frequency narrow band light source emits a coherent light.

According to some embodiments of the invention, the adjustable frequency narrow band detector includes: a light deflector having a frequency dependent angle of deflection, the light deflector receiving an incident light beam and producing a deflected beam; a sensor array including a plurality of sensors, each of the plurality of sensors positioned, to receive the deflected beam at a different respective deflection angle corresponding to a respective narrow frequency band; the each sensor incremented from a base state to an exposed state by exposure to the deflected light of the respective narrow frequency band; the controller further configured for adjusting a frequency sensitivity of the detector to the narrow reception band by activating at least one target sensor of the plurality of sensors; the target sensor positioned to receive the deflected light corresponding to the narrow reception band; the controller further configured for setting to the base state at least one other sensor while the target sensor is activated; for example the other sensor may be deactivated and/or may be neighboring to the target sensor.

According to some embodiments of the invention, the system further includes: a plurality of reset circuits, each circuit of the plurality of reset circuits for setting at least one proper subset of the plurality of sensors to the base state, and wherein the each reset circuit is operationally controlled by the controller.

According to some embodiments of the invention, the system further includes: at least one reset circuit for setting at least some of the plurality of sensors to the base state, and at least one switch for connecting a proper subset of the plurality of sensors to the reset circuit wherein the at least one switch is operationally connected to and controlled by the controller.

According to some embodiments of the invention, each circuit of the plurality of reset circuits connects the proper subset of the plurality of sensors to a ground.

According to some embodiments of the invention, the light source is configured to emit a narrow band light having a bandwidth less than $\frac{1}{10}$ the bandwidth of a full spectrum of the light source.

According to some embodiments of the invention, the light source is configured to emit a narrow band light having a bandwidth less than 5 nm.

According to some embodiments of the invention, the detector is configured to have a narrow band sensitivity having a bandwidth less than $\frac{1}{10}$ the bandwidth of a full spectrum sensitivity of the detector.

According to some embodiments of the invention, the detector is configured to be sensitive to light in a narrow band having a bandwidth less than 5 nm.

According to an aspect of some embodiments of the invention, there is provided a method of increasing depth sensitivity of an OCT module comprising: emitting light over a plurality of narrow illumination wave-bands, each narrow illumination wave-band emitted at a specified time and reaching a detector at a corresponding time; dividing the light along a sample path and a reference path; receiving light from both the sample and the reference paths at a detector; synchronizing a frequency sensitivity band of the detector at the corresponding time to overlap the each illumination wave-band at the specified time and analyzing the output from the detector to derive a depth distribution of reflectance of a sample.

According to some embodiments of the invention, emitting is of a coherent light.

According to some embodiments of the invention, emitting is of a narrow band light having a bandwidth less than $\frac{1}{10}$ the bandwidth of a full spectrum of the light source.

According to some embodiments of the invention, emitting is of a narrow band light having a bandwidth less than 5 nm.

According to some embodiments of the invention, the synchronizing includes configuring the detector with the sensitivity band having a bandwidth less than $\frac{1}{10}$ the bandwidth of a full spectrum sensitivity of the detector.

According to some embodiments of the invention, the synchronizing includes configuring the detector with the sensitivity band having a bandwidth less than 5 nm.

According to some embodiments of the invention, the detector includes a sensor array, the sensor array including a plurality of sensors, the method further comprising: deflecting the signal at a frequency dependent angle; activating a first sensor of the plurality of sensors the first sensor positioned to be exposed to light deflected at a angle corresponding to the sensitivity band; setting a second sensor to a base state while the first sensor is in the activated state.

According to some embodiments of the invention, the setting includes connecting the second sensor to a reset circuit.

According to some embodiments of the invention, the setting includes connecting the second sensor to a ground.

According to some embodiments of the invention, the method further comprises: exciting the first sensor from the base state to an excited state according to a light intensity in the sensitivity band after the setting.

According to some embodiments of the invention, the method further comprises: also exciting the second sensor from the base state to an excited state according to a light intensity in another frequency band after the setting.

According to some embodiments of the invention, the method further comprises: resetting the first sensor to the base state simultaneous to the also exciting.

According to some embodiments of the invention, the deflecting includes at least one action selected from the group consisting of diffracting the incident light and refracting the incident light.

According to an aspect of some embodiments of the invention, there is provided a adjustable frequency narrow band optical detector comprising: a sensor array including a plurality of sensors a light deflector having a frequency dependent angle of deflection, the light deflector receiving an incident light beam and deflected each frequency band of a plurality of narrow frequency bands to a corresponding sensor of the plurality of sensors; a controller adjusting a frequency sensitivity of the detector to a preferred frequency by activating at least one target sensor corresponding to the preferred frequency while setting to a base state at least one other sensor of the sensor array; the other sensor corresponding to another frequency band.

According to some embodiments of the invention, the at least one other sensor neighbors the at least one target sensor.

According to some embodiments of the invention, the detector further includes: a plurality of reset circuits, each circuit of the plurality of reset circuits for setting at least one proper subset of the plurality of sensors to the base state, and wherein the each reset circuit is operationally connected to and controlled by the controller.

According to some embodiments of the invention, the detector further includes: at least one reset circuits for setting at least some of the plurality of sensors to the base state, and at least one switch for connecting a proper subset of the plurality of sensors to the reset circuit wherein the at least one switch is operationally connected to and controlled by the controller.

According to some embodiments of the invention, the reset circuit connects the at least some sensors to a ground.

According to some embodiments of the invention, at least one of the sensors is a solid state photodetector.

According to some embodiments of the invention, at least one of the solid state photodetectors is a GaAs detector.

According to some embodiments of the invention, at least one of the solid state photodetectors is a Si detector.

According to an aspect of some embodiments of the invention, there is provided a method of reducing noise while detecting an narrow band signal comprising: deflecting an incident light signal at a frequency dependent angle; receiving a deflected light from the signal on a sensor array, the sensor array including a plurality of sensors wherein each of the sensors is positioned for the receiving in a narrow wave band of the deflected light; activating a first sensor of the sensor array, the first sensor positioned to receive the deflected light in a preferred frequency band; setting a second sensor to a base state while the first sensor is in the activated state.

According to some embodiments of the invention, the setting includes connecting the second sensor to a reset circuit.

According to some embodiments of the invention, the setting includes connecting the second sensor to a ground.

According to some embodiments of the invention, the method further comprises: exciting the first sensor from the base state to an excited state according to a light intensity in the preferred frequency band after the setting.

According to some embodiments of the invention, the method further comprises: also exciting the second sensor from the base state to an excited state according to a light intensity in another frequency band after the setting.

According to some embodiments of the invention, the method further comprises: resetting the first sensor to the base state simultaneous to the also exciting.

According to an aspect of some embodiments of the invention, there is provided a system for reducing clutter when measuring a spectrum comprising: an adjustable frequency narrow band light source emitting an emitted light toward a sample; an adjustable frequency narrow band detector positioned to receiving a narrow band signal generated by the sample in response to the emitted light; a controller configured for controlling the light source to emit light over a succession narrow frequency bands, synchronize the detector to be sensitive to a narrow reception band that overlaps the narrow band signal when the narrow band signal reaches the detector, and analyzing the output from the detector to derive the spectrum.

According to some embodiments of the invention, the controller is configured to synchronize the detector and the light source by tuning the detector to be sensitive to a narrow band overlapping the emitted band of the light source.

According to some embodiments of the invention, the adjustable frequency narrow band light source emits a coherent light.

According to some embodiments of the invention, the adjustable frequency narrow band detector includes: a light deflector having a frequency dependent angle of deflection, the light deflector receiving an incident light beam and producing a deflected beam; a sensor array including a plurality of sensors, each sensor of the plurality of sensors positioned, to receive the deflected beam at a different respective deflection angle, each respective deflection angle corresponding to a narrow frequency band; the each sensor incremented from a base state to an exposed state by exposure to the deflected light deflected at the respective angle; wherein the controller is further configured for adjusting a frequency sensitivity of the detector to the narrow reception band by activating at least one target sensor of the plurality of sensor positioned for exposure to the deflected light at an angle of the deflection corresponding to the narrow reception band; the controller further setting to the base state at least one other sensor of the plurality of sensors, the other sensor neighboring to the target sensor, the setting of the other sensor simultaneous to the activating of the target sensor.

According to some embodiments of the invention, the system further comprises: a plurality of reset circuits, each circuit of the plurality of reset circuits for setting at least one proper subset of the plurality of sensors to the base state, and wherein the each reset circuit is operationally controlled by the controller.

According to some embodiments of the invention, the system further includes: at least one reset circuit for setting at least some of the plurality of sensors to the base state, and at least one switch for connecting a proper subset of the plurality of sensors to the reset circuit wherein the at least one switch is operationally connected to and controlled by the controller.

According to some embodiments of the invention, the at least one reset circuit connects the at least some sensors to a ground.

According to some embodiments of the invention, at least one of the sensors is a solid state photodetector.

According to some embodiments of the invention, the light source is configured to emit a narrow band light having a bandwidth less than 1/10 the bandwidth of a full spectrum of the light source.

According to some embodiments of the invention, the light source is configured to emit a narrow band light having a bandwidth less than 5 nm.

According to some embodiments of the invention, the detector is configured to have a narrow band sensitivity having a bandwidth less than 1/10 the bandwidth of a full spectrum sensitivity of the detector.

According to some embodiments of the invention, the detector is configured to be sensitive to light in a narrow band having a bandwidth less than 5 nm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1A:
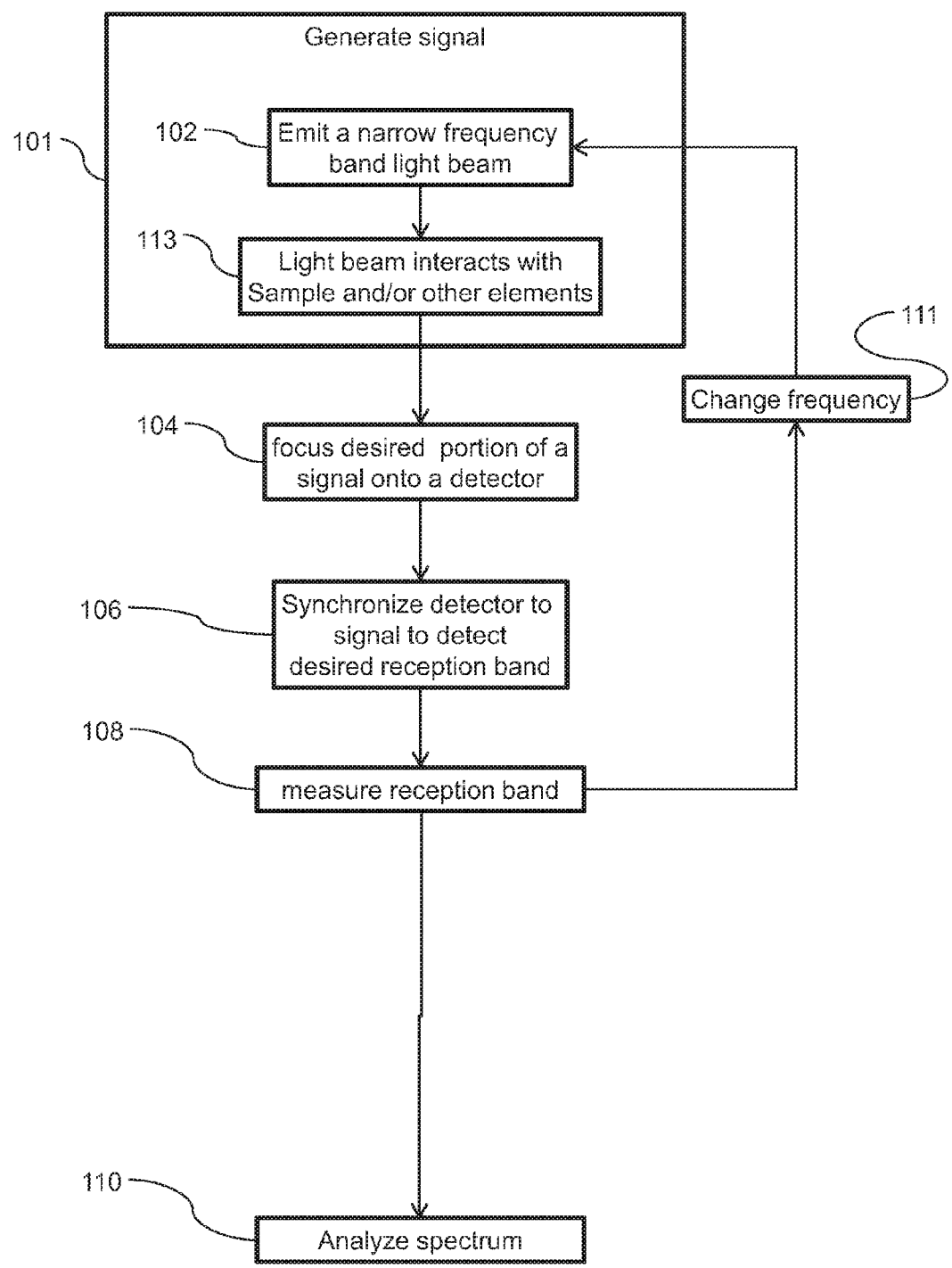
FIG. 1A-1B are a flow chart illustrations of methods of reducing clutter in a spectral scanning device in accordance with some embodiments of the current invention.

The present invention, in some embodiments thereof, relates to an adjustable frequency band optical detector and, more particularly, but not exclusively, to a system for high resolution optical coherence tomography (OCT).

Overview

An aspect of some embodiments of the current invention relates to synchronizing an adjustable frequency light source and an adjustable frequency detector. Synchronizing a narrow detector band with a narrow light source band may facilitate for sharp spectral detection. For example, synchronizing a narrow source band and/or a narrow band detection sensitivity may reduce "spill over" of clutter and/or noise between spectral bands. In some embodiments, reducing noise and/or a signal clutter, may improve the quality of the spectral detection. In some embodiments, improved spectral detection may facilitate improved image quality and/or depth discrimination in Optical Coherence Tomography (OCT). Optionally an improved discrimination OCT probe may be used to perform an in-vivo biopsy.

Some embodiments, the present invention may include performing Fourier domain optical coherence tomography. For example, an adjustable frequency narrow band light source may be used to emit narrow frequency band pulses over various frequencies of a spectrum. The narrow band pulses may interact with a sample and/or a interferometer to generate a narrow band signal. An adjustable frequency narrow band detector may be synchronized to the light source to detect the narrow band signal and/or reject noise outside of the narrow signal band. For example, the light source and detector may simultaneously sweep a across one or more wavelengths of a spectrum. Alternatively or additionally, multiple bands may be emitted and/or detected simultaneously. Alternatively or additionally, spectral bands may be sampled in any order (not just sweeping across the spectrum). Alternatively or additionally, synchronizing of a detector and a light source may account for a delay between emission of light at the light source and reception of the light at the receiver. Alternatively or additionally, light may be emitted and received substantially simultaneously.

In some embodiments, an OCT system includes directing a light beam from a light source to a sample and to a reference path, recombining the reference and sample beams to a recombined signal, and detecting the combined signal. For example, according to an embodiment of the present invention, the combined signal is received by an adjustable frequency narrow band detector. Optionally the detector is synchronized to a narrow band beam from the light source and/or a narrow band signal. For example, synchronization may include tuning a detector to a band that has synergistic noise reduction and/or clutter reduction with the narrow band source illumination and/or the narrow band signal from the sample. A full spectral interferogram over a broad spectral bandwidth may be obtained by combining data from multiple narrow band interferograms.

In some embodiments, a bandwidth [for example the Full width at half maximum (FWHM)] of a narrow frequency illumination may range for example between 0.1 to 1 nm and/or 1 to 5 nm and/or 5 to 10 nm and/or 10 to 20 nm and/or 20 to 50 nm and/or 50 to 100 nm. In some embodiments a sensor may be sensitive to a narrow band over a width for example between 1 to 5 nm and/or 5 to 10 nm and/or 10 to 20 nm and/or 20 to 50 nm and/or 50 to 100 nm. In some embodiments a spectrum may include between 10 to 50 bands and/or between 50 to 80 bands and/or between 80 to 150 bands.

In some embodiments, a full spectrum may span frequencies between 50 to 100 nm and/or between 100 to 250 nm and/or between 250 to 500 nm and/or between 500 to 750 nm and/or between 750 to 1000 nm and/or 1000 and 1500 nm. In some embodiments a scan rate may range for example between 10 Hz to 100 Hz and/or between 0.1 kHz to 1 kHz and/or between 1 kHz to 15 kHz and/or between 15 kHz to 30 kHz and/or between 30 kHz to 100 kHz and between 100 to 1000 kHz. For example, a narrow band may have a width ranging between $\frac{1}{10}$ to $\frac{1}{20}$ and/or $\frac{1}{20}$ to $\frac{1}{50}$ and/or $\frac{1}{50}$ to $\frac{1}{100}$ and/or $\frac{1}{100}$ to $\frac{1}{1000}$ and/or $\frac{1}{1000}$ to $\frac{1}{10000}$ of the full spectrum being scanned.

In some embodiments, the overlap between an emitted light band and/or a received frequency band is adjusted during each pulse time period and/or between periods. For example, the detector will have a high sensitivity to the desired signal and low sensitivity to noise in the light signal. Alternatively or additionally, the overlap may be adjusted such that during each pulse time period, light in wavelength that causes clutter in the detector is generated at a very low intensity or not at all. Synchronizing the light generator and detector may allow measuring of a spectrum with increased signal to noise and/or decreased clutter.

In some embodiments of an Optical Coherence Tomography system, a measured spectrum is used to produces a depth profile. Improved spectral sharpness may optionally result in improved depth discrimination. Optionally a spatial scanner is used to produce a complete 3D image of a portion of tissue. For example, a 3D image may be reconstructed as is known in the art. For example, improved depth resolution may facilitate resolution of small structure. For example, in some embodiments depth resolution may range between 0.1 and 0.5 microns and/or 0.5 to 1.0 microns and/or 1 to 2 microns and/or 2 to 5 microns. For example, resolution of below 1 micron may facilitate recognition of cancerous changes in cells. Optionally, a high resolution OCT probe may be used to diagnose cancerous cells in-vivo without removing samples. Optionally or additionally, an in-vivo OCT probe may scan a volume of tissue. For example, an OCT probe may be used to detect and/or diagnose prostate cancer in-vivo.

In some embodiments of the present invention a single lumen may be used to facilitate OCT scanning and/or therapeutic access to nearby and/or overlapping regions. Optionally, OCT imaging and/or OCT scanning and/or other diagnostic procedures and/or other detection procedures and/or therapeutic procedures may share a single access tube and/or a single lumen for sequential and/or repeated and/or simultaneous access to a region of interest ROI. Alternatively or additionally there may be multiple lumens accessing the ROI. Optionally facilitating multiple and/or coordinated access may allow improved control and/or evaluation of medical procedures. Control and/or evaluation is optionally in real time and/or during a procedure.

Some embodiments of the present invention include scanning OCT systems. For example a scanning OCT system may include a means and/or method for combining scan information from a plurality of access tubes and/or from a plurality of tissue insertions of same access tube, recording information in a common unified three-dimensional coordinate system. The tools and/or methodology may facilitate scanning and/or recording information from a tissue volume larger than that which can be scanned by a single access. OCT systems according to some embodiments of the present invention may be used to combine, coordinate, and/or collectively analyze information gleaned from OCT scans performed at a plurality of positions and/or during a plurality of "tissue insertions" (insertion of access tube into tissue for scanning purposes). The plurality of tissue insertions may optionally be performed by one access tube in a plurality of sequential insertions, and/or by (optionally simultaneous) insertions of a plurality of access tubes into tissue. Both methods may facilitate use of OCT to scan a large tissue volume. In this manner, in some embodiments, an entire organ, such as for example a prostate, can be scanned in sufficient detail to detect clinically significant tumors or other lesions. Scanning in-vivo may facilitate analysis of larger volumes and/or portions of an organ than ex-vivo analysis.

In some embodiments, a detailed three-dimensional mapping and/or modeling of a lesion, optionally obtained from a plurality of access tube insertions into a lesion and/or into tissue around a lesion may provide a detailed guide for a surgical procedure. Alternatively, such a map and/or model may provide means for a series of detailed anatomical comparisons of views of a ROI over time.

Some embodiments of the present invention may include one or more localization indicators. For example, a localization indicator may include a position and/or orientation sensor. Alternatively or additionally, a localization indicator may include a marker (for example a marker that can be seen using fluoroscopy and/or other imaging technology). In some embodiments an indicator may include a relative position indicator. For example, an indicator may include a radio indicator for a local positioning system and/or a beacon and/or an indicator of relative position between an access tube and/or a tool. For example, a window may have markers that allow a user to determine where an OCT image is with respect to the position of an access tube and/or the access tube may include a localization indicator (for example the indicator may have 1, 2, 3, 4, 5, or 6 degrees of freedom).

In some embodiments, a tool sized and shaped to fit into the access tube may have an indicator of position relative to the access tube (for example length of insertion and/or relative rotational orientation) and/or a tool may have an indicator of position relative to a local object (for example a marker in the body of a patient and/or a fixed marker in an operating theater). Optionally an access tube and/or tool may include a position indicator on a distal location (for example at the tool location in the patient) and/or at a proximal location (for example in a handset and/or handle of the tool and/or access tube). For example a position indicator may include a five or six degrees of freedom (DOF) assembly sensor. For example a location sensor may include sensor models 55, 90, 130, 180 and/or 800 available from Ascension Technology Corporation, 6221 Shelburne Road, Suite 130, Shelburne, Vt. 05482, USA. Alternatively or additionally, a position indicator may include a fiducial marker for example an implants such as FlexiCoil™, PolyMark™ or Gold Soft Tissue markers, available from Civco 2301 Jones Blvd, Coralville, Iowa 52241.

In some embodiments, a tunable light source may include, a sampled grating based semiconductor laser. Such a laser may have two sections, of which one is the lasing section incorporated with a sampled grating that can enable the sweeping of the wavelengths, and the other is an optical amplifier section that can compensate for the change in the output optical power. Alternatively, the tunable light source can also be made from a tunable Fabry-Perot semiconductor cavity. Such a laser can also have two sections, of which one is a gain section for lasing and the other is a transparent section for sweeping the lasing wavelengths. A separate optical amplifier can also be made next to the laser to boost and also control the optical output power. Furthermore, the tunable laser can also be made from a tunable ring or race-track semiconductor cavity. Such a laser can again have two sections, of which one is a gain section for lasing and the other is a transparent section for sweeping the lasing wavelengths. A separate optical amplifier can also be made next to the laser to boost and control the optical output power.

Other types of light sources for some embodiments of the present invention include for example an extended multi-wavelength cavity laser that is made tunable with at least an optical amplifier and a tunable filter functioning as part of the laser cavity. The extended long laser cavity is optionally made with optical fiber. Both the optical amplifier and tunable multi-wave length filter are optionally either integrated optical waveguide based, or optical fiber based or optical fiber pig tailed.

In some embodiments an adjustable frequency narrow band detector may include a multi-channel detectors and/or an array detector. For example an adjustable frequency narrow band detector may include a monolithically integrated semiconductor multi-channel receiver, and/or a discrete optical demultiplexer and/or a series of thin film band pass filters that can be combined with a series of photo detectors to function as the multi-channel receiver.

An aspect of some embodiments of the current invention relates to an adjustable frequency narrow band detector with reduced clutter. Optionally a detector may include an array detector wherein a first portion of the sensors of the array are activated to detect a signal while a second portion of the sensors of the array are deactivated, for example to reduce sensitivity to noise and/or clutter.

In some embodiments deactivating a sensor include and/or consist of preparing the sensor for a new measurement. For example, deactivating may include and/or consist of zeroing the sensor, setting the sensor to a base state, grounding the sensor, inhibiting the sensor from accumulating charge, inhibiting the sensor from moving to an excited state and/or shading the sensor.

In some embodiments, the timing of deactivating of a sensor may depend on the type of sensor and/or the properties of the sensor and/or the signal being measured.

In some embodiments, a detector may include a frequency dependent light deflector (for example a grating and/or prism). For example, the deflector may direct each wavelength in a different direction. The detector optionally includes focusing optics directing each of wavelength (and/or wave band) onto a different element and/or a different sensor of a detector array. For example there may exist a one to one correspondence between a specific wave band and/or wave length $BG_i$ and/or $\lambda_i$ and a specific sensor $S_i$. Alternatively or additionally, a single wave band may be directed at a plurality of sensors. In some embodiments, when a particular wavelength and/or band is being detected on a corresponding element (for example a sensor and/or a set of sensors) in the sensor array, other array elements are turned off and/or drained and/or zeroed and/or desensitized and/or reset and/or set to a base state and/or blocked.

In some embodiments, a specific band may be shaded and/or blocked by a liquid crystal display LCD with one or more LCD elements. The LCD may have a separately controlled area for each sensor set and/or may block any given sensor set.

In some embodiments, before detecting a particular wave band, the sensors corresponding to the band are drained and/or zeroed (for example set to a base state) and/or desensitized and/or reset.

The size of a sensor is optionally related to the detected wave length. For example the detected wavelength may range between 1 to 10 microns. In some embodiments the detected wave length may be between 10 to 100 microns and/or between 100 to 1000 microns and/or between 1 to 5 millimeters and/or between 5 to 50 mm. In some embodiments, an OCT engine utilizing a larger wavelength may give a larger focal length and/or greater depth penetration. In some embodiments, an OCT engine utilizing a smaller wavelength may give a more precise depth discrimination.

In some embodiments, a GaAs type sensors may be used, for example for signals in the IR spectrum. Alternatively or additionally, Si sensors may be used, for example in the visible and/or short IR range. Optionally a detector may include active-pixel sensors for example made in a CMOS process. Alternatively or additionally, a detector may include a charged coupled device CCD. Alternatively or additionally a detector may include a cryogenic sensor and/or a particle detector. Alternatively or additionally a detector may include an HgCdTe detector, for example in the IR range. Alternatively or additionally a detector may include a light emitting diode, for example acting as a photo detector by reverse biasing. Alternatively or additionally, a detector may include a photoresistor and/or light dependent resistor (LDFR) and/or a photovoltaic cell and/or a photodiode and/or a photomultiplier tube and/or a phototube and/or a phototransistor, and/or a quantum dot photoconductor and/or a semiconductor detector.

In some embodiments, a bandwidth [for example the Full width at half maximum (FWHM)] of a narrow frequency sensitivity of a single sensor and/or set of sensors may range for example between 0.1 to 1 nm and/or 1 to 5 nm and/or 5 to 10 nm and/or 10 to 20 nm and/or 20 to 50 nm and/or 50 to 100 nm. In some embodiments a sensor array may include between 10 to 50 and/or between 50 to 80 sensors and/or between 80 to 150 and/or between 150 to 500 and/or between 500 to 1000 sensors and/or sensor sets. For example the frequency sensitivity of a single narrow band element may range between 1/10 to 1/20 and/or between 1/50 to 1/100 and/or between 1/100 to 1/1000 of the full spectral sensitivity band of the entire array and/or detector. Optionally, each sensor and/or sensor set may be individually resettable and/or independently connected to a reset circuit. Alternatively or additionally, a plurality of sensor sets may be reset together. For example a detector may include between 5 to 10 and/or between 10 to 50 and/or between 50 to 150 and/or between 150 to 1000 independent reset circuits.

In some embodiments, the sensitivity band of the entire sensor array and/or detector may span frequencies between 50 to 100 nm and/or between 100 to 250 nm and/or between 250 to 500 nm and/or between 500 to 750 nm and/or between 750 to 1000 nm and/or 1000 and 1500 nm. In some embodiments a scan rate may range for example between 10 Hz to 100 Hz and/or between 0.1 kHz to 1 kHz and/or between 1 kHz to 15 kHz and/or between 15 kHz to 30 kHz and/or between 30 kHz to 100 kHz and between 100 to 1000 kHz.

For simplicity of exposition, electromagnetic waves used by OCT probes, a detector and/or a light source will sometimes be referred to herein as "light", but it is to be understood that wavelengths including visible light, Near-infrared (IR) wavelengths, other IR wavelengths and/or microwave wavelengths are also being referred to in references herein to "light" used in OCT probes.

In some embodiments, an OCT module comprises a probe, and/or an OCT engine and/or motors, and/or optionally other equipment classically used to operate an OCT probe and/or to derive image data from the probe. Optionally the prove is insertable in a body for example of a human and/or an animal and/or an object, Alternatively or additionally a probe may direct and/or detect a light signal from outside a human, an animal and/or an object, For example the OCT engine may include one or more light sources, sensors, light guides, beam splitters, polarizing elements, filters, circulators, lenses and/or graded index fibers—GRIN (for example a fiber optic coupler). Elements of the OCT engine may optionally separate the light along a sample and reference path and/or an interferometer. As used herein, when appropriate according to context, the term "OCT probe" should be understood to include the probe itself and all other necessary parts of an OCT probe module required to operate it.

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Some embodiments of the invention may include one or more of the following components:
VCSEL=vertical-cavity surface-emitting laser, or VCSEL; SLD=Superluminescent Diodes for example delivering stable, broad wavelengths from 750 nm to 1620 nm with short coherence lengths, fiber optic sensors, and optical test instruments; BS=Beam Splitter; R=reference signal; D=Detector; S=Sample Tissue.

Scanning Method with Reduced Clutter

Figure 1B:
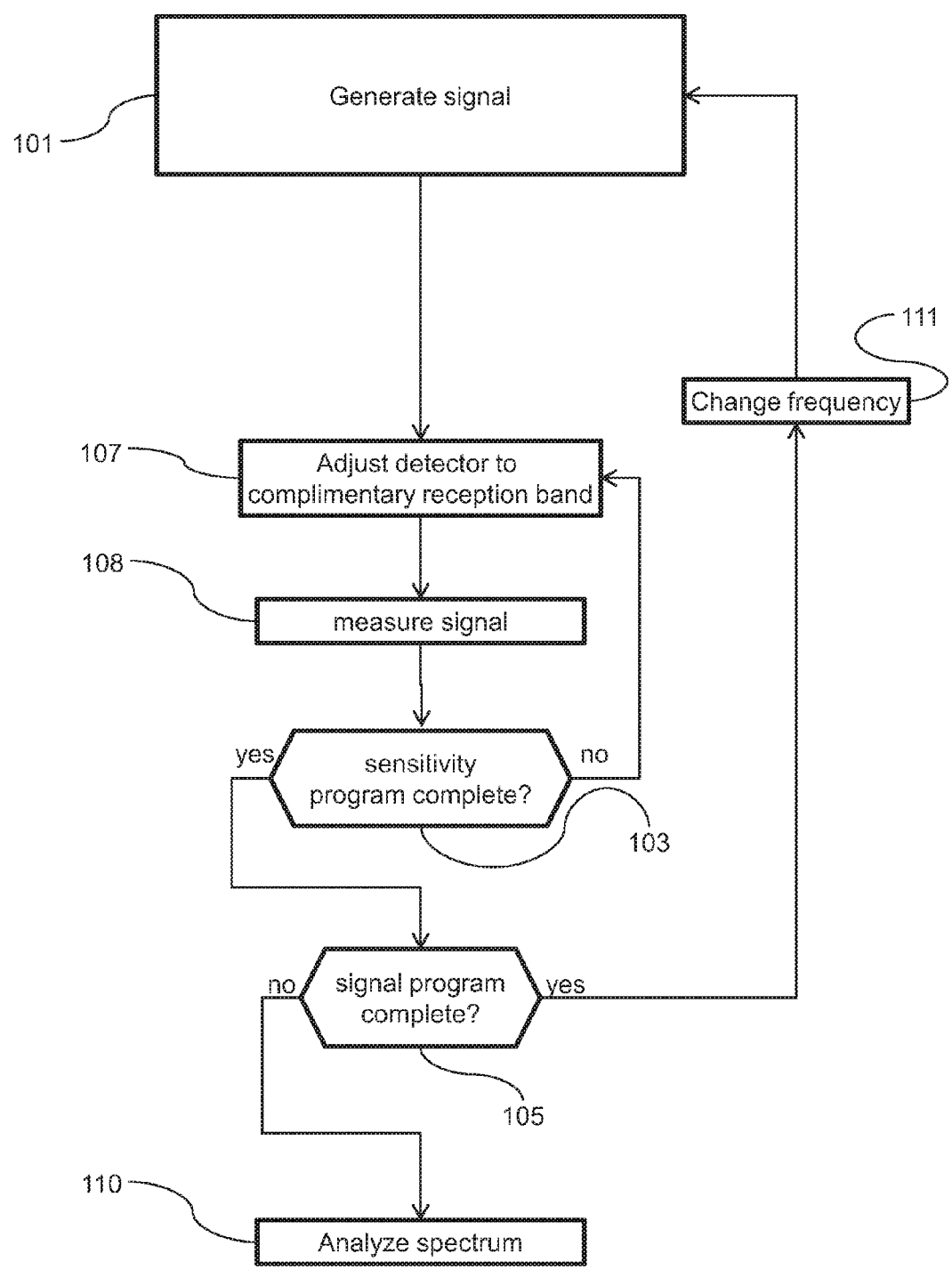

Referring now to the figures, FIGS. 1A-1B are flow chart illustrations of methods of reducing clutter and/or noise in a spectral scanning device in accordance with some embodiments of the current invention. For example an adjustable frequency narrow band light source may be synchronized with an adjustable frequency narrow band light detector. In some embodiments, the detected signal is the overlap of the generated band and/or the sensitivity band of the detector. For example, the detector may be tuned to have a low sensitivity in a band of high noise amplitude. Additionally or alternatively the signal generator (for example a light source in reaction with a sample and/or a reference light path) may be tuned to reduce the intensity of noise in a non-desired band at which the detector has a high sensitivity (a clutter band). Optionally the band generated by the source and/or band detected by the detector are co-tuned to have an overlapping zone at the desired detection frequency and/or a high sensitivity to the desired band and/or to reduce noise and/or to reduce clutter. A spectral scanning device may synchronously adjust the detector and/or light source over time to measure a sequence of frequency bands. For example, the scanning device may produce a spectrum wherein each frequency band is measured at reduced clutter and/or noise. Alternatively or additionally, a frequency band may be measured multiple times with different adjustments of the light source and/or detector. For example the multiple measurements may be combined and/or the combined measurements may reduce noise and/or clutter when compared to each single measurement.

In some embodiments, the system performs a double and/or dual spectral selection of frequency. For example, one or more wavelength bands are emitted by a source and/or generated by an engine. A detector is synchronized to the emitted and/or generated wavelengths. For example, light may be deflected such that the desired light (for example at the emitted and/or generated wavelength) falls on particular sensor which is activated. Non-desired light optionally falls onto other sensors which are deactivated.

FIG. 1A illustrates a method of reducing noise and/or clutter in measurement of a spectrum including synchronizing a signal generator and a signal detector to emit and/or detect a narrow band signal in accordance with an embodiment of the present invention. Optionally, a scanning light source is used to emit light in a desired narrow band and/or to emit light that reacts with a sample to generate a narrow band signal. The signal will optionally stimulate a narrow band a detector. Optionally the detector and signal generator are synchronized together in accordance with an embodiment of the current invention. For example, for each signal being generated, the light source is tuned to generate the signal with increased signal and/or reduced noise. Optionally, for each signal being generated, the detector is tuned to increase a sensitivity to the desired signal and/or to reduce sensitivity to noise and/or clutter.

In some embodiments, a signal generator may be tuned to generate 101 a detector signal. For example, a signal generator may be tuned to expose of a particular property and/or location of a sample. For example, an OCT engine may be tuned generate 101 a signal exposing a reflectance of a particular depth layer in a sample. For example a tunable light source may emit 102 narrow band light beam. The light beam may optionally interact 113 with an interferometer and/or the sample to generate a signal. For example the interferometer may use destructive interference to reduce intensity of light in the narrow band reflected from depths other than the sample depth. Thus, the signal focused on the detector may be enhanced to improve signal to noise for a reflectance from the desired sample location and/or depth. Optical focusing elements may be used to focus 104 the light beam onto the sample and/or focus 104 the signal onto the detector. When a signal is received by a detector, the detector may be adjusted 106 to increase sensitivity to the desired signal and/or to decrease sensitivity to noise. For example, the detector is tuned to increase sensitivity to the desired frequency band and/or to decrease sensitivity to spurious bands which may reflect from other depths in the sample and/or other locations in the sample and/or be generated in other ways. In some embodiments, after a first signal has been generated 101 and/or measured 108, a second signal may be generated 101 and/or measured 108. For example, the second signal may expose a different aspect and/or location of the sample. For example, to generate 101 the second signal, a beam frequency may be changed 111. For example, in OCT changing 111 the frequency, optionally changes the depth intervals that are reduced by the interferometer. Optionally, changing the frequency includes tuning both the light source and the detector to the new frequency. After measuring signals over a spectrum of wave lengths, properties at one or more depth intervals in the sample may be estimated by analyzing 110 the measured spectrum of light signals.

FIG. 1B illustrates a method of reducing noise and/or clutter in measurement of a spectrum by synchronizing a signal generating engine and/or a detector synergistically in accordance with an embodiment of the present invention. In some embodiments, the signal may not be tuned reduce all noise and/or may be tuned to reduce particularly noise in a band that will affect the detector. Optionally, the signal generating engine may generate noise in a band to which a detector has a low or no sensitivity and/or the signal generating engine may be adjusted to reduce noise in a band to which the detector is particularly sensitive. For example, a signal may be biased to a frequency higher than a desired frequency and/or a detector may be tuned to a complementary frequency that is lower than the desired frequency. The interaction between the band of the detector and/or the signal may result in an improved overall signal to noise at the desired frequency. Optionally, multiple measurements may be made with different signals and/or detector sensitivities. The multiple measurements may be combined to produce an improved spectral measurement.

In some embodiments, there may be a program of measurements for example including different detector sensitivities and/or signal properties. For each measurement the source light beam and/or the detector sensitivity may be adjusted (for example tuned). Different measurements may be combined (for example during analysis 110 of the spectrum) to give an improved estimate of the sample properties. For example, after a measurement of a particular signal with a particular set of detector properties, if 103 there is another desired set of properties in the program of measurements with the same particular signal, the detector may be adjusted 107 (for example with a different sensitivity band) and another measurement 108 made. Optionally, if 105 there are more signal properties in the signal program, a different signal is generated 101 and measured 108. Optionally, the results of a single measurement 108 may be analyzed 110 (for example combined with other measurements) to estimate more than one spectral band.

For example, in some embodiments, it is desired to detect a signal is in a desired band BGd. The signal source may be tuned such that the light arriving at the detector includes a signal in the desired band BGd and noise BGn in a non-desired band. The detector is optionally tuned to have a sensitivity to the desired band BRd and a clutter sensitivity in an undesired band BRn. Optionally the signal source and/or detector are tuned so that the signal noise BGn is in a band with low detector sensitivity BRn.

Detection with Reduced Clutter

Figure 2:
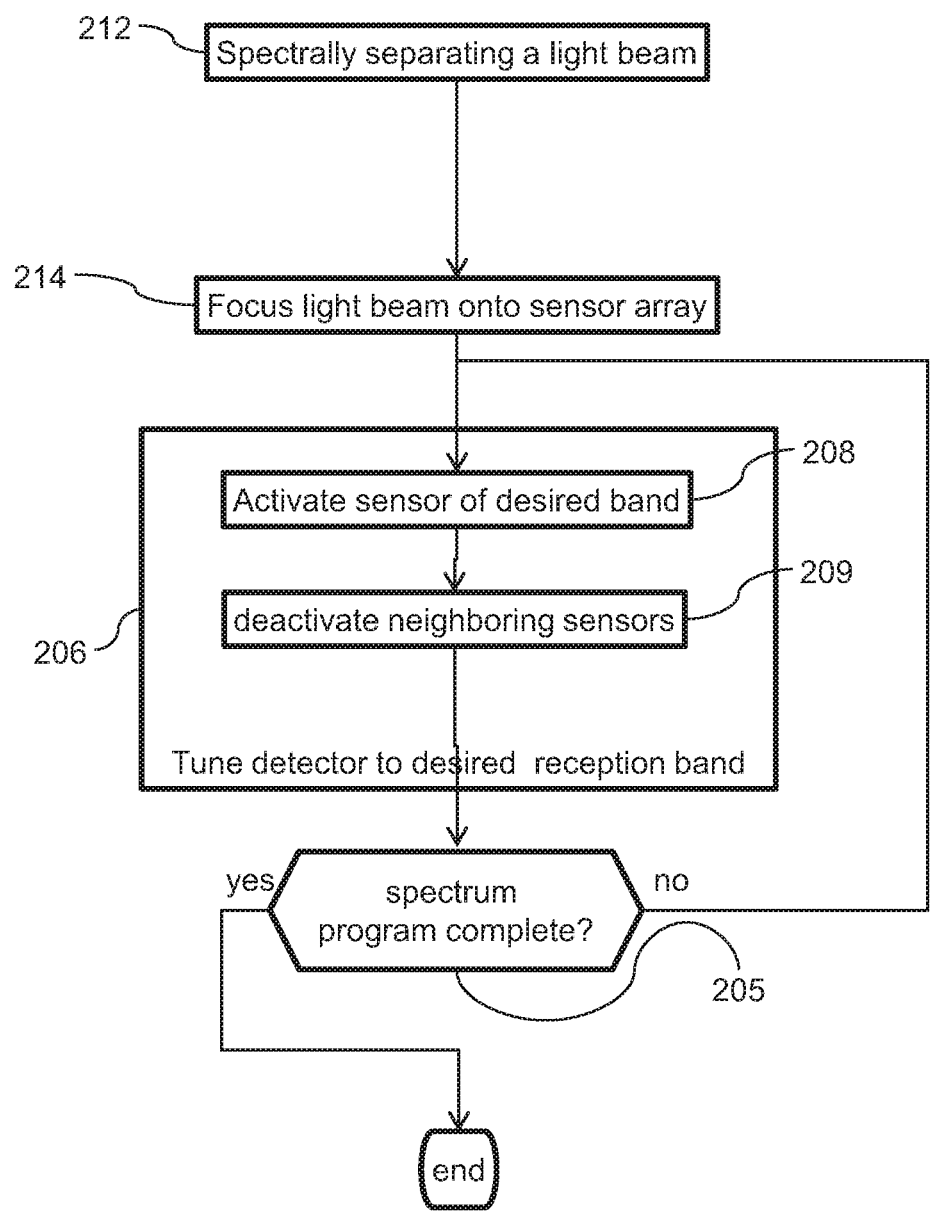
FIG. 2 is a flow chart illustration of a method reducing clutter in detection a narrow band light signal with a multiband detector in accordance with an embodiment of the present invention.

FIG. 2 is a flow chart illustration of a method reducing clutter in detection of a narrow band light signal and/or a spectrum in accordance with an embodiment of the current invention. For example, the narrow band signal may be detected by a multiband detector. For example, a light beam may be separated spectrally into a plurality of spectral bands. The separated beam may be focused 214 onto a sensor array. For example, each band may be focused onto and/or directed at a different sensor and/or a different set of sensors. All or some of the sensors may be reset before being used to measure a signal. For example, while one set of sensors is being used to measure a first signal another set of sensors may be reset.

In some embodiments a light beam may be separated 212 into separate spectral bands. In some embodiments, a light deflector (for example a grating and/or a prism) may deflect each spectral band at a different angle. Each spectral band is optionally focused 214 onto a respective sensor and/or set of sensors in a sensor array. In some embodiments, while measuring a signal on a first sensor on a first band, noise may affect a sensor of a signal on another band. Optionally, a detector may be tuned 206. For example tuning 206 may nullify noise from sensors and/or light falling on sensors measuring an undesired band when the detector is measuring a signal in a different desired band. For example, while measuring a signal in a first band, the sensors corresponding to the measured band may be activated 208 and/or sensors corresponding to other bands may be deactivated 209 and/or reset. Optionally sensors corresponding to a particular band may be reset just prior to measuring that band. To measure a spectrum, different light bands may be measured simultaneously and/or sequentially.

In some embodiments, a first set of sensors may be activated 208 then a measurement may be made in a first band using the first set of sensors. Optionally, previous to the measurement, the first set of sensor may have been reset and/or deactivated 209. In some embodiments, a second set of sensors may be reset and/or shielded and/or deactivated 209, for example while a measurement is being made with the first set of sensors. Afterwards the second set of sensors may be activated 208 and/or used to measure a second band of the light. In some embodiments, there may be a dead time where there is no measurement while one or more sensors is being reset and/or deactivated and/or activated. For example, the timing of deactivating and/or activating and/or measuring may depend on the properties of the sensor. For example, for a sensor that requires a ramp up period when going from a deactivated state to an activated state, there may be a dead time when the light source is off while the sensor is ramping up. Alternatively or additionally, for a sensor requiring a ramp up time between the deactivated and activated states, the system may jump from far away band to far away band. For example, for a case of five bands arranged consecutively B1, B2, B3, B4, B5, while a measurement is made on band B1, a neighboring band B2 may be deactivated, but bands B2-B5 may be active. Then a measurement may be made on band B4 while bands B3 and B5 are deactivated and band B2 is ramping up. Then a measurement may be made on B2 with B1 and B3 deactivated and B5 ramping up. Then a measurement may be made on B5 while B4 is deactivated etc. The order and/or timing of measurement, activation and/or resetting may arranged to account for, for example, the sensitivity, the amount of noise and/or crosstalk, the number of bands that need to be deactivated to avoid noise and/or cross talk, the amount of time it takes to make a measurement, the amount of time it takes to reset a sensor and/or the amount of time it takes to ramp up a sensor.

In some embodiments, a spectrum may be measured 205 by serially measuring different bands and/or building a spectrum for the individual measurements. Measuring bands separately and/or resetting particularly sensors before measuring a corresponding band may lead to reduced interaction (cross talk) between sensors and/or lead to less noise and/or more accurate measurements of the spectrum.

Reduced Clutter OCT Engine

Figure 3:
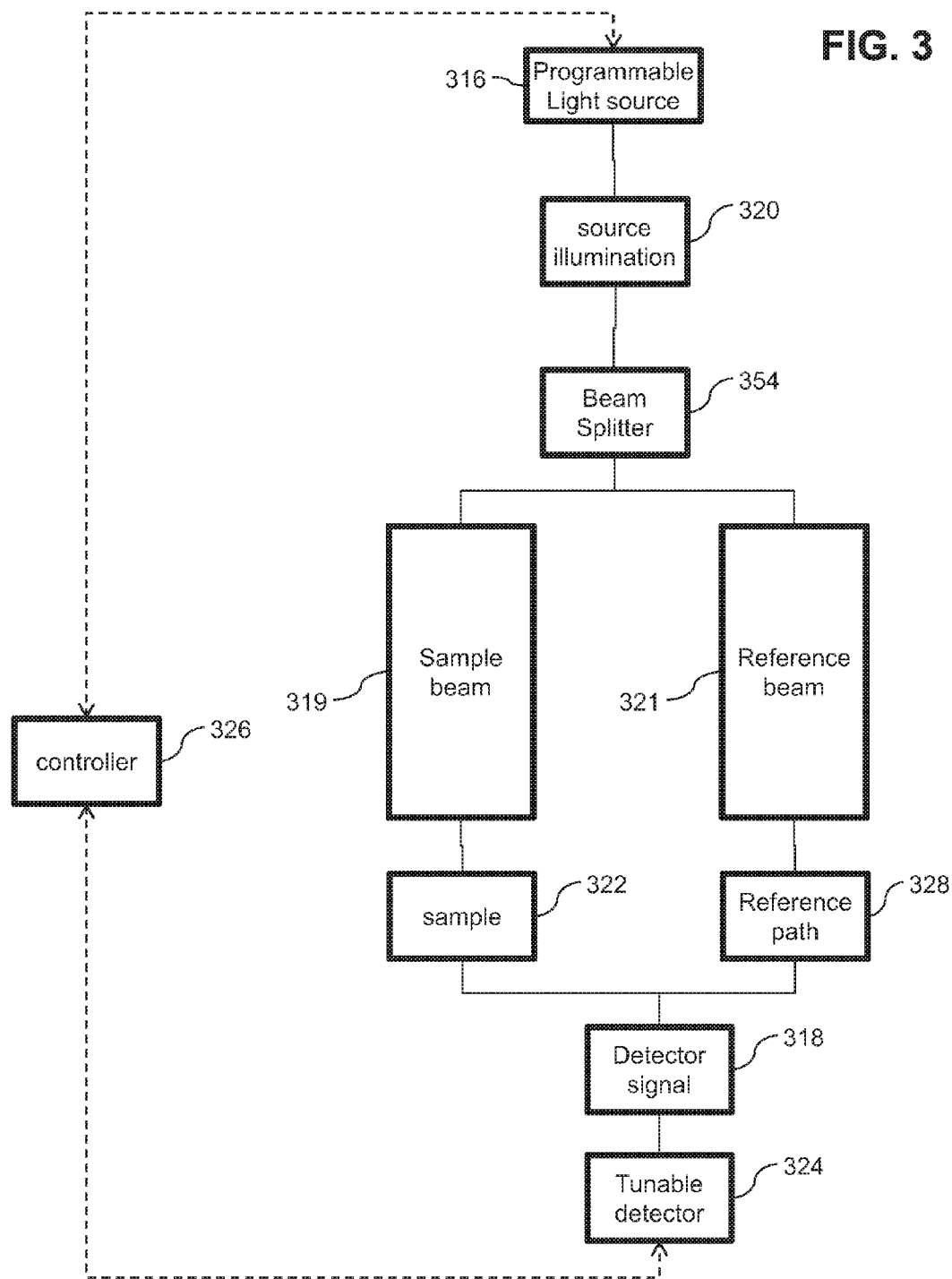
FIG. 3 is a block diagram of an OCT engine in accordance with an embodiment of the present invention.

FIG. 3 is a block diagram of an OCT engine in accordance with an embodiment of the present invention. In some embodiments, a controller 326 synergistically synchronizes a programmable narrow band light source 316 and/or a tunable detector 324 to emit, generate and/or measure a particular signal and/or to reduce the intensity of and/or sensitivity to noise and/or spurious signals.

In some embodiments, a programmable light source 316 is supplied to emit a source illumination 320. For example, light source 316 may emit a narrow band and/or coherent light beam. Optionally, light source 316 is programmable in that the frequency band of the emitted light changes according commands from controller 326. For example, light source 316 may include a vertical-cavity surface-emitting laser (VCSEL). In some embodiments, light source 316 includes a high speed swept source with a sweep rate of at least about 20 kHz that is continuously tunable over a broad tuning range (preferably greater than 50 nm).

Some embodiments may include a beam splitter. Optionally, the beam splitter splits the source illumination into a sample beam 319 and/or a reference beam 321. Optionally sample beam 319 is reflected off a sample 322 and/or reference beam 321 travels down a reference path 328 and back to detector 424. Reference beam 321 and sample beam 319 may be reunited to form a detector signal 318. In some embodiments, interference between reference beam 321 and sample beam 319 may result in different depths of the sample being exposed by different wavelengths of detector signal 318. A tunable detector 324 may then be used to measure a spectrum of detector signal 318.

In some embodiments, controller 326 may command light source 316 to emit a narrow beam source illumination 320 that sweeps over time across a desired wide band spectrum. Synchronously, as the narrow band source illumination 320 arrives at detector 324 as detector signal 318, controller 326 may command detector 324 to detect a narrow band that overlaps, includes and/or is included in the narrow source illumination 320 band. Synchronously, as the narrow band source illumination 320 arrives at detector 324 as detector signal 318, controller 326 optionally commands detector 324 to detect complementary band to the narrow source illumination 320 band. For example, the detector band may overlaps, include and/or be included in the narrow source illumination 320 band.

Figure 4:
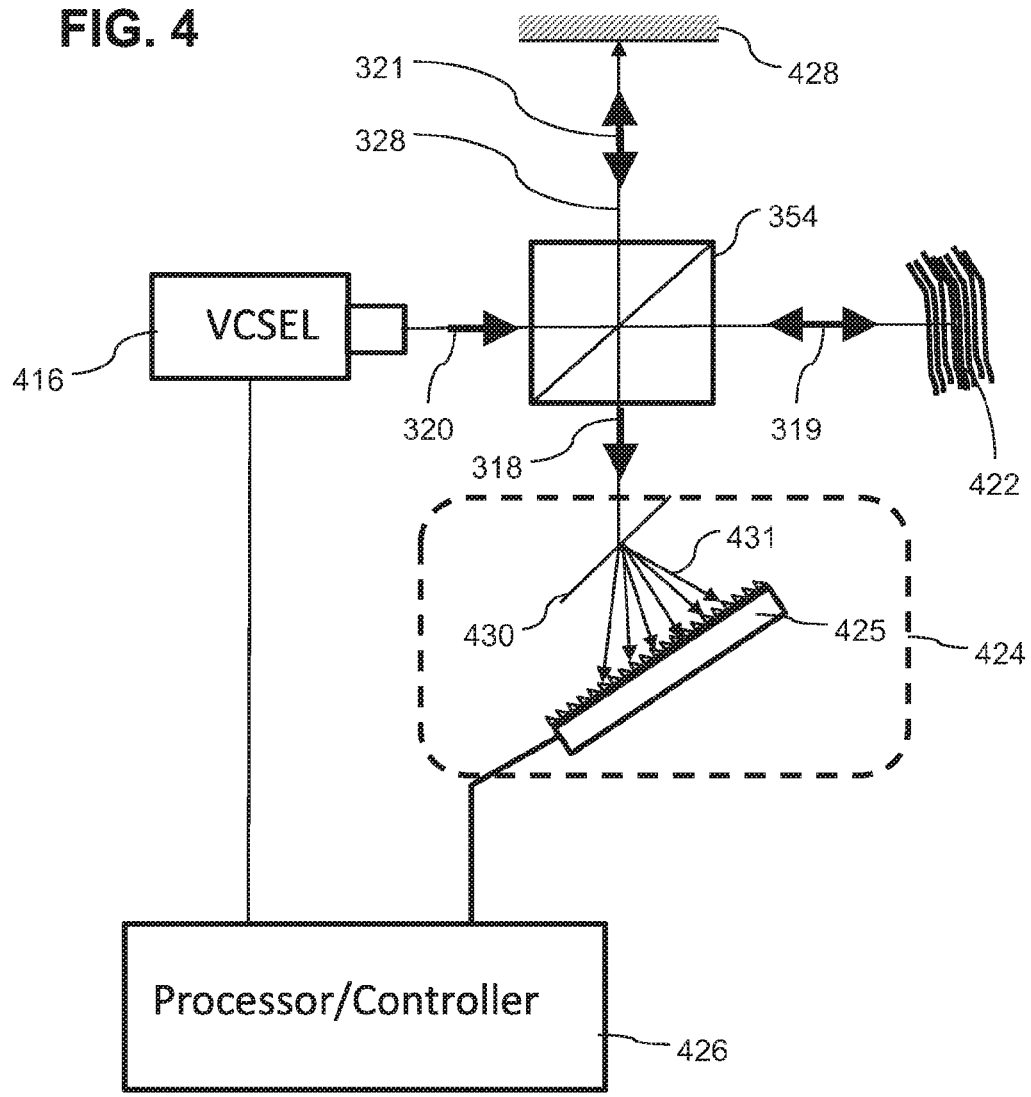
FIG. 4 is a schematic diagram of an OCT system in accordance with an embodiment of the present invention.

FIG. 4 is a schematic diagram of an OCT system in accordance with an embodiment of the present invention. In some embodiments a narrow band tunable light source 416 may include a VCSEL. Source 416 is optionally synchronized with a tunable detector 424 by a controller 426. For example, detector 424 may include a light deflector 430. For example deflector 430 may separate detector signal 318 into frequency bands 431, for example by refracting and/or diffracting the light by a frequency dependent angle. The each frequency band 431 is optionally focused along a path onto one or more respective sensors from a sensor array 425. Optionally, detector 424 is tuned by zeroing sensors that are not in the path of the desired frequency band (for example that are not in the path of narrow band of source illumination 320). Optionally controller 426 controls the sensitivity of detector 424 (for example by resetting, zeroing, activating and/or deactivating one or more sensors of sensor array 425). Optionally controller 426 receives output from detector 424 and/or processes the output to compute a spectrum).

In some embodiments, reference beam 321 may travel up reference path 328 to a reflector 428 and/or be reflected back down reference path 328. For example, reference beam 321 may travel back down reference path 328 and/or through beam splitter 354 and/or to a beam combiner (for example anther beam splitter).

In some embodiments, sample beam 319 may be reflected off a sample 422. Sample 422 optionally reflects sample beam 319 back to beam splitter 354 and/or a beam combiner (for example anther beam splitter). Optionally the returning sample beam 319 and reference beam are combined (for example by beam splitter 354 to form detector signal 318.

Reduced Clutter Detector

Figure 5:
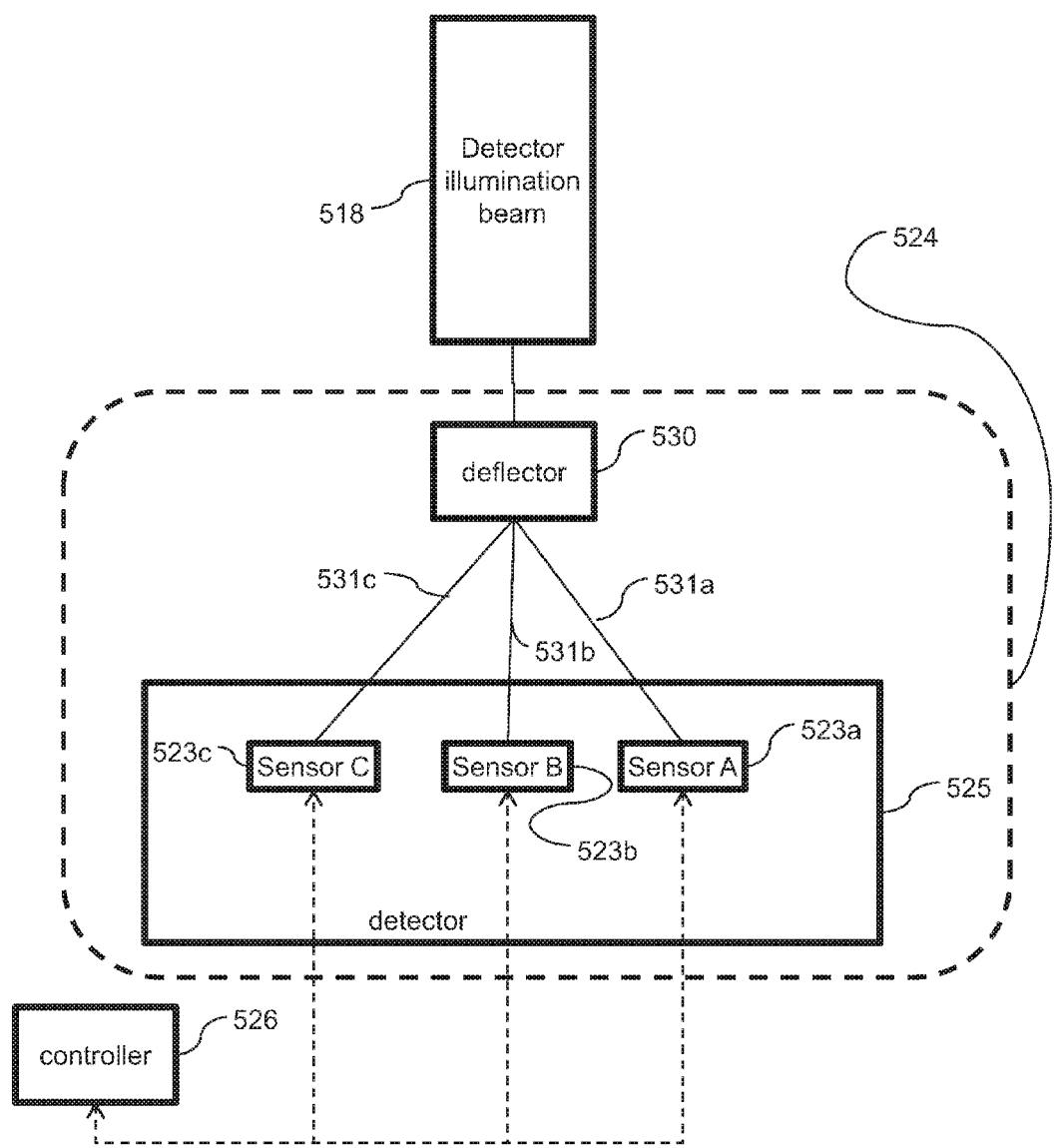
FIG. 5 is a block diagram of an adjustable frequency optical detector in accordance with an embodiment of the present invention.

FIG. 5 is a block diagram of an adjustable frequency optical detector in accordance with an embodiment of the present invention. In some embodiments a light deflector 530 may separate a signal 518 into frequency bands 531$a$, 531$b$ and 531$c$, for example by refracting and/or diffracting the light by a frequency dependent angle. Each frequency band 531$a$, 531$b$ and 531$c$ is optionally focused onto one or more respective sensors 523$a$, 523$b$ and 523$c$ from a sensor array 525. Optionally, detector 524 is tuned by zeroing sensors that do not correspond to the desired frequency band. Optionally a controller 526 controls the sensitivity of detector 524 (for example by resetting, zeroing, activating and/or deactivating one or more sensors of sensor array 525). Optionally controller 526 receives output from detector 524 and/or processes the output to compute a spectrum). For example, controller 526 may have separate control circuits and/or software control keys and/or commands and/or addresses to zero, ground, activate and/or deactivate each sensor set of sensors 523$a$-523$c$.

In some embodiments, controller 526 tunes detector 524 to receive the desired signal while being relatively insensitive to noise and/or spurious signals. For example when a narrow band source illumination and/or a desired narrow band signal 518 corresponds to detector band 531$b$, controller 526 will zero sensors 523$c$ and/or 523$a$ while activating and/or receiving output from sensors 523$b$.

Figure 6:
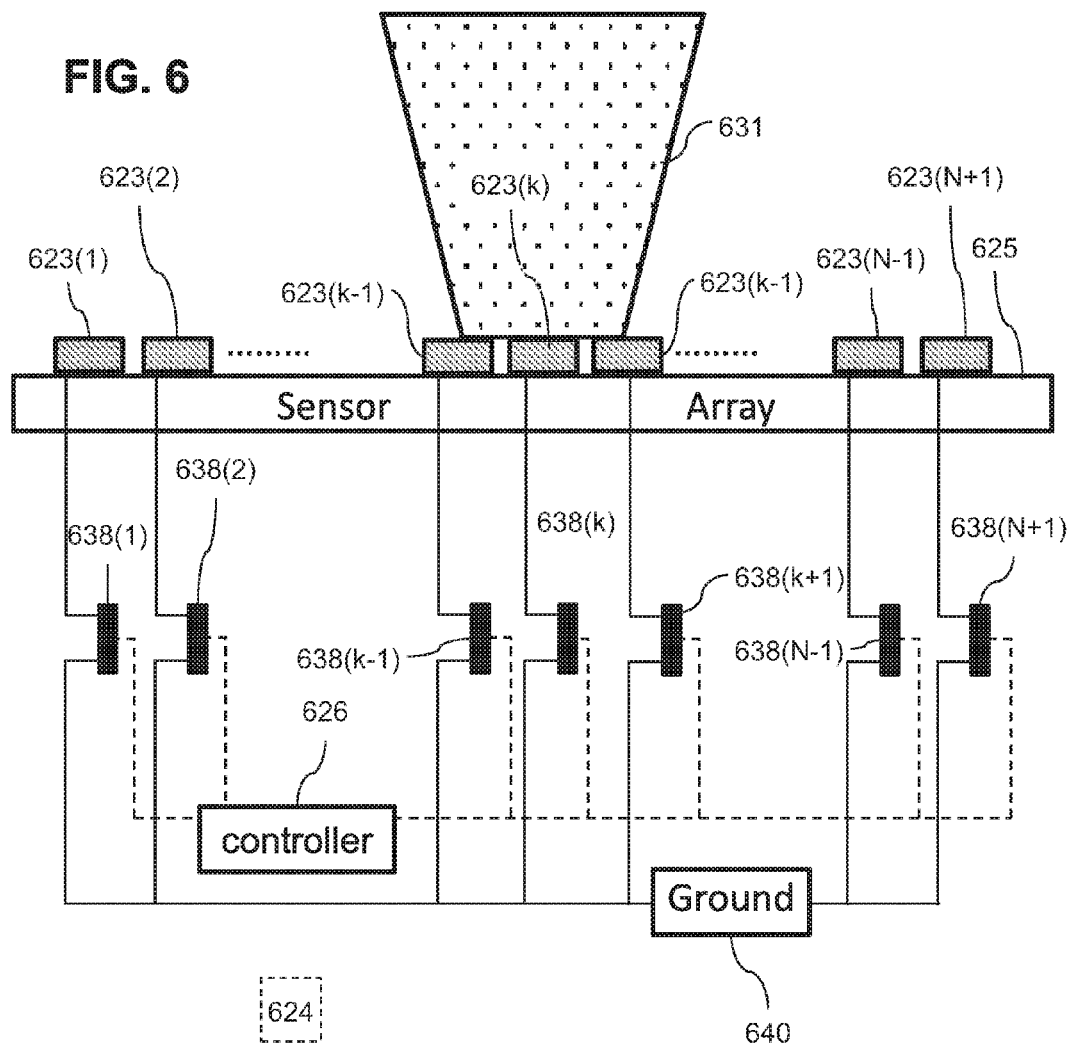
FIG. 6 is a schematic diagram of an adjustable frequency band optical detector in accordance with an embodiment of the present invention.

FIG. 6 is a schematic diagram of an adjustable frequency band optical detector 624 in accordance with an embodiment of the present invention. For example, a sensor array 625 includes a plurality of sensor sets 623($i$) for i=1 to N (each sensor set 623($i$) may include one or more sensors). Each sensor set 623($i$) is connected to independently to a controller 626 and/or corresponding reset circuit 638($i$). When a desired signal 631 is of a band that corresponds to a particular sensor, for example 623($k$), neighboring sensors, for example 623($k$−1) and/or 623($k$+1) are zeroed and/or reset.

In some embodiments, some or all of sensors 623($i$) may include a sensor element incorporating a reset switch or gate that is reset for example by grounding. Optionally, each reset circuit 638($i$) connects a corresponding sensor 623($i$) to a ground 640. Optionally each circuit 638($i$) includes a MOFSET switch controlled by controller 626. For example, to sensitize a sensor [for example sensor 623(*i*)] and/or to allow a sensor [for example sensor 623(*i*)] to function, a corresponding switch [for example 638(*i*)] is opened allowing sensor 623(*i*) to collect charge. Optionally, to zero and/or reset a sensor [for example 623(*i*−1) and/or 623(*i*+1)] a corresponding switch [for example 638(*i*−1) and/or 638(*i*+1)] is closed grounding and/or draining charge from the sensor [for example 623(*i*−1) and/or 623(*i*+1)].

In some embodiments, a separated light band beam 631 may illuminate an intended sensor [for example sensor 623(*k*)] and/or a non-intended sensor [for example sensors 623(*k*−1) and/or 623(*k*+1)] (for example illuminating a non-intended sensor may be result from imprecise optics, mis-alignments, noise in the signal for example including unintended frequencies for example resulting from a finite band width associated with each specific wavelength. In some embodiments, nullifying, zeroing and/or resetting unintended sensors [for example sensors 623(*k*−1) and/or 623(*k*+1)], may reduce sensitivity of detector 624 to noise and/or clutter.

In some embodiments, multiple separate bands may be detected at the same time. For example, multiple sets of sensors corresponding to the signal may be activated at the same time while sensors that neighbor the activated sensors may be nullified. For example active sensor sets may be separated by a minimum number of deactivated sets ranging for example between 1 to 3 and/or from 3 to 10 and/or from 10 to 50 and/or from 50 to 200.

Reduced Clutter OCT System

Figure 7A:
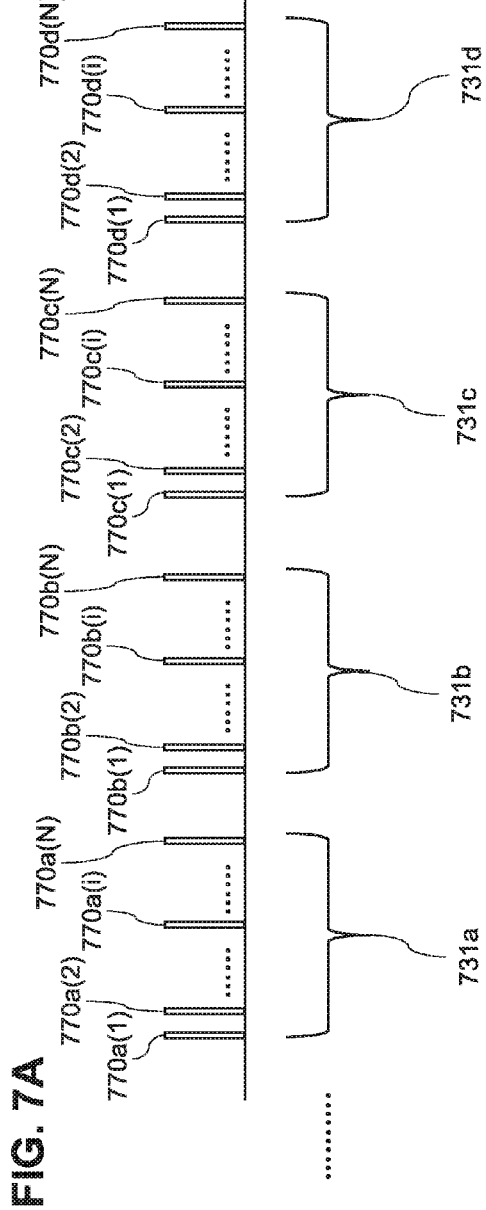
FIGS. 7A and 7B are schematic diagrams of a method of generating an OCT image in accordance with an embodiment of the present invention.

FIG. 7A is a schematic diagram of a detector signal train of a OCT engine in accordance with an embodiment of the current invention. Optionally a programmable light source (for example VCSEL 716 as illustrated for example in FIG. 7B) emits a train of light pulse sets 731*a*, 731*b*, 731*c*, 731*d*. Each pulse set 731*a*-731*d* includes for example N pulses 770*a*(1)-770*d*(N). For example, each pulse 770*a*(*i*), 770*b*(*i*), 770*c*(*i*), 770*d*(*i*) consists of a narrow bandwidth coherent light pulse. Optionally each set 731*a*-731*d* includes the same pattern of N different frequency pulses 770*a*(*i*), 770*b*(*i*), 770*c*(*i*), 770*d*(*i*) for i=1 to N. Alternatively or additionally the pattern of frequency of pulses may differ for different sets 770*a*-770*d* of pulses. For example, different frequency pulses 770*a*(1)-770*d*(N) may expose different depths into the sample. Optionally multiple sets 770*a*-770*d* of pulse may be directed at one location in the sample. For example, repeated sets 770*a*-770*d* may be used to get average values for different pulses of the same frequency 770*a*(*i*)-770*d*(*i*) at one location. Alternatively or additionally, different sets 770*a*-770*d* of pulses may be directed at different locations in the sample. For example, repeated sets 770*a*-770*d* may be used to map different locations in the sample.

Figure 7B:
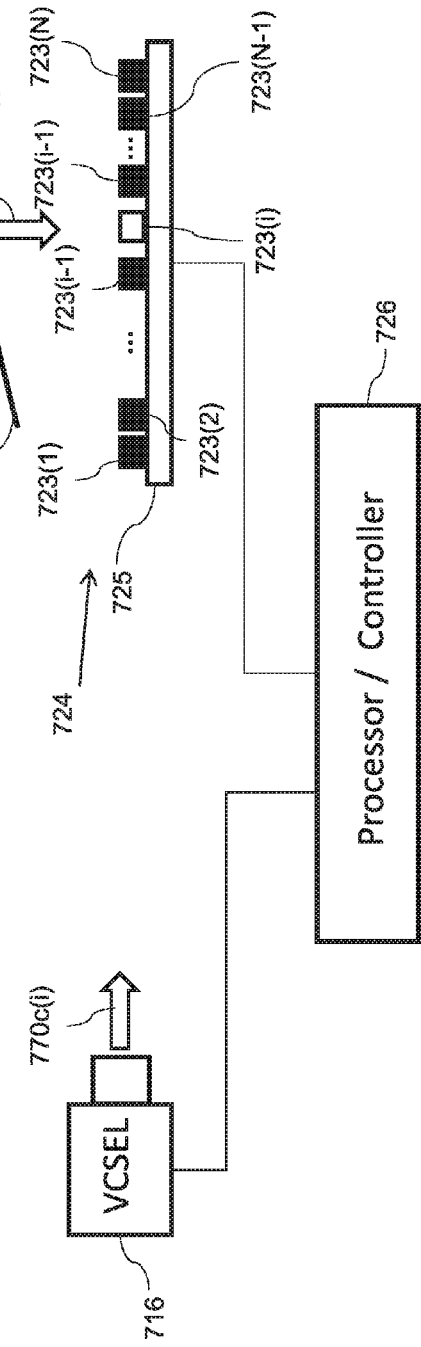

FIG. 7B is a schematic diagram of a OCT engine in accordance with an embodiment of the current invention. Optionally a controller 726 synchronizes a programmable light source (for example VCSEL 716) and a detector 724.

In some embodiments the light source emits over time a train of pulses of coherent narrow band light pulses [for example 770*a*(1) to 770*d*(N) as illustrated in FIG. 7B]. In some embodiments, each pulse from the light source [for example pulse 770*c*(*i*)] reflects off a sample and/or passes along a reference path to a detector 724 as a detector signal [for example detector signal 770*c*(*i*)']. As each light pulse 770*a*(1)-770*d*(N) reaches detector 724, controller 726 optionally adjusts detector 724 to be sensitive to light in a narrow band that is the intended measurement band. For example, detector signal 770*c*(*i*)' reaches a frequency dependent light deflector 730 and/or is directed according to frequency to a sensor set 723(*i*) of an array 725 of sensor sets 723(1)-723(N). For example, light at the intended sample frequency is directed toward sensor set 723(*i*) and/or spurious light including for example light at other frequencies is directed towards sensor sets 723(1)-723(1-*i*) and/or sets 723(*i*+1)-723(N). Optionally, when signal 770*c*(*i*) reaches detector 724, controller 726 deactivates sensor sets 723(1)-723(1-*i*) and/or sets 723(*i*+1)-723(N). Optionally, deactivating sensor sets in un-desired frequencies reduces noise and/or clutter in the measurements of detector 724. Optionally, when and/or before the next pulse in the pulse train comes to processor deactivates sensors that are in the un-desired frequency range [optionally including sensor 723(*i*)] and/or activates a desired sensor. For example, for the next pulse 770*c*(i+1) processor 726 activates sensor 723(*i*+1) and deactivates all of the other sensors.

Figure 8:
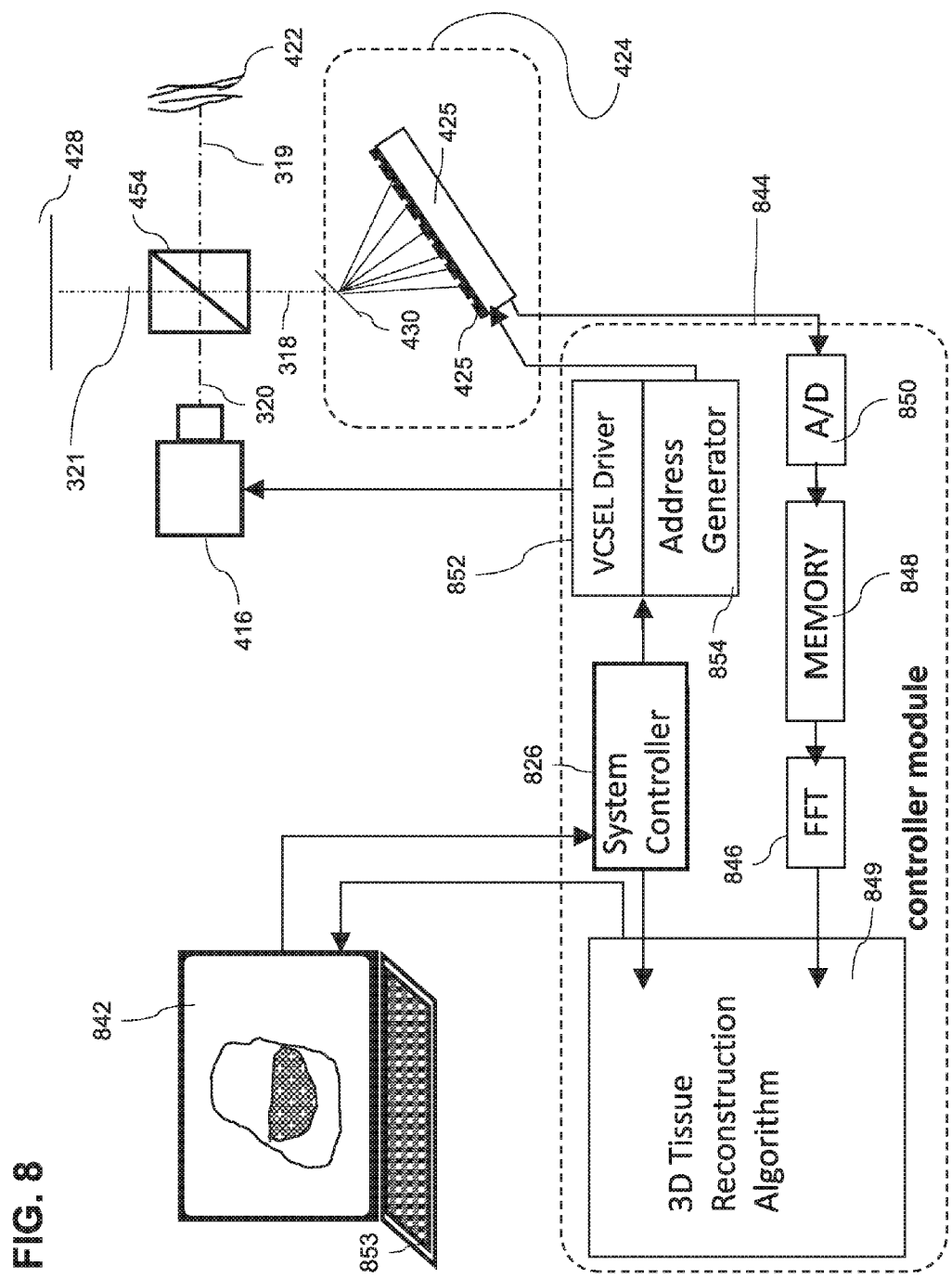
FIG. 8 is a schematic diagram of an OCT system in accordance with an embodiment of the present invention.

FIG. 8 is a schematic overall view of an OCT tissue diagnostics system in accordance with an embodiment of the current invention. In some embodiments, the system includes and OCT Engine based on conventional beam splitter 454 and/or a fiber optic splitter. Optionally the light source includes a tunable VCSEL 416. VCSEL 416 is optionally synchronized by a controller module 844 with a detector 424. For example controller module 844 activates one sensor set at a time that corresponds to the specific wavelength emitted by VCSEL 416. The signal group is processed as known in the art by Fourier transform software 846 to develop a tissue profile at one image point ("A mode"), if a complete image is desired, the single view may be scanned point by point and/or virtual reconstruction can be used to map the diagnosed tissue.

In some embodiments controller module 844 may include data acquisition software and/or hardware (for example an analogue-digital converter A/D 850 and/or memory 848. Optionally memory 848 may include volatile and/or non-volatile memory, and/or a portable memory device and/or media and/or an internal memory). In some embodiments controller module 844 may include image generating software 849. In some embodiments controller module 844 may include a VCSEL driver 852 and/or an address generator 854 (for example address generator 854 may direct which sensor to activate or deactivate). In some embodiments the controller module 844 may include a user input interface 853 and/or a user output interface 842. User input interface 853 and/or a user output interface 842 may optionally be hard-wired to controller module 844 and/or connected through a wireless connection and/or a network. For example, User input interface 853 and/or a user output interface 842 may include a personal computing device (for example a smart-phone and/or a personal computer).

In some embodiments, sequencing address generator 854, that may optionally be included in controller module 844. Address generator 854 optionally initiates a train of command pulses in groups of N. Optionally, each of the N command pulses corresponding to a different wavelength (and/or a narrow wave band). For example a pulse "i" of a group corresponds to a wave length, λi (i=1 ... N) of a group of illumination pulses. For example, each command pulse of the group triggers the generation of a light pulse of wavelength around, λi. Optionally the light pulse may have a narrow generated bandwidth $BG_i$. For example a temporal sequence of command pulses may result in temporal sequence of light pulses. In some embodiments, detector 424 detects light in a received band $BR_i$. Optionally, detector 424 will be synchronized to light generator 416 such that $BR_i$ overlaps $BG_i$ near λi.

Figure 9:
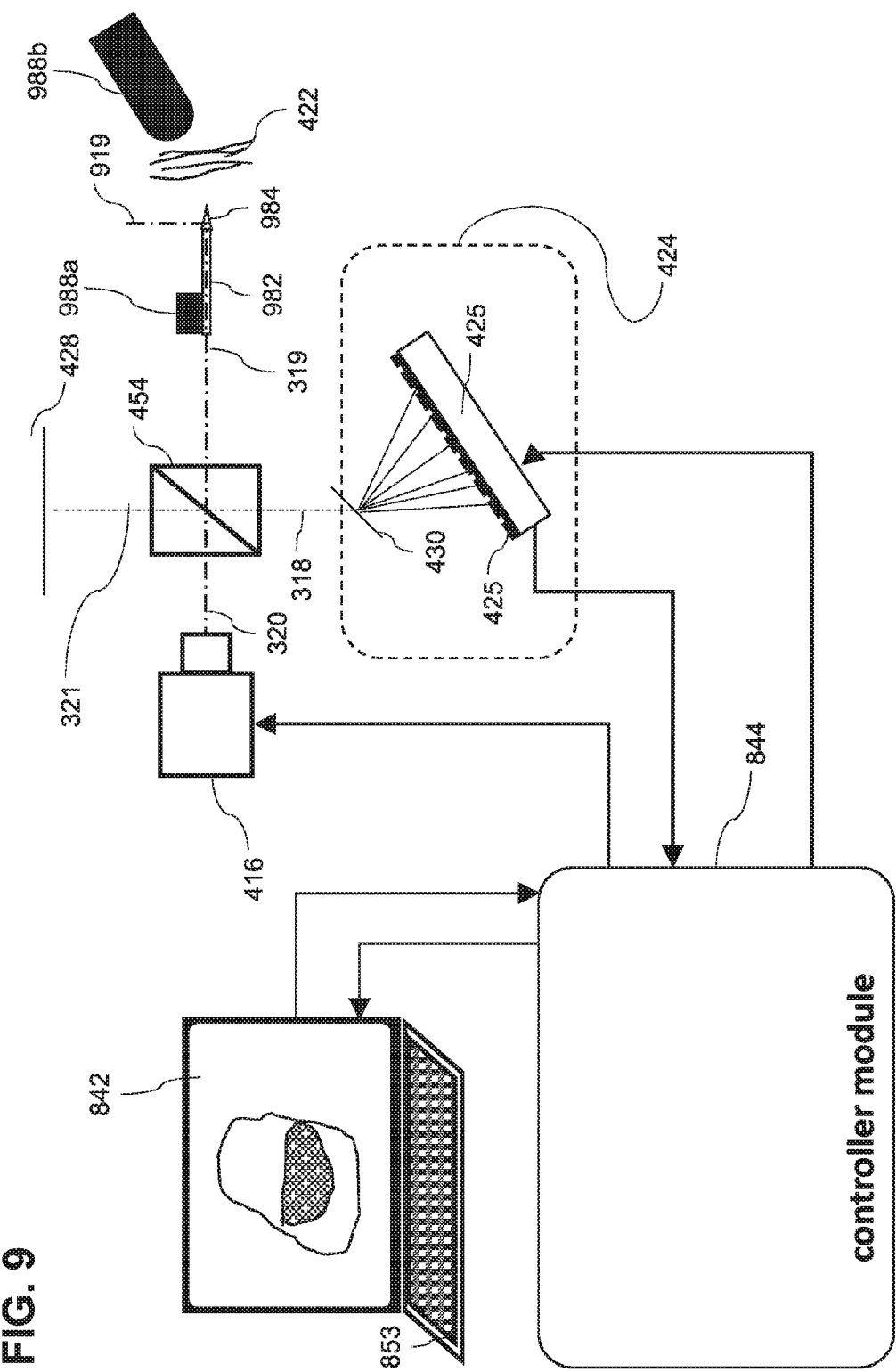
FIG. 9 is a schematic diagram of an OCT probe module in accordance with an embodiment of the present invention.

FIG. 9 is a schematic overall view of an OCT in vivo tissue biopsy system in accordance with an embodiment of the current invention. In some embodiments, sample beam 319 scans tissue within a living subject.

In some embodiments sample beam 319 is delivered into a living subject (for example a human patient) with a probe 982. For example, probe 982 may include a biopsy needle. Optionally, probe 982 includes a scanning head 984. For example, scanning head 984 may redirect sample beam 319 into different locations of the sample without moving probe 982. For example, scanning head 984 may rotate an angle of a projecting sample beam 919 inside sample 422. Optionally an integral localization sensor 998a (for example including a position and/or an orientation sensor) and/or an external localization sensor 988b (for example including a ultrasound device and/or a fluoroscope) may give a position of probe 982 and/or scanning head 984 and/or beam 919 with respect to a fixed reference and/or a moving reference and/or a part of the patient.

Optionally, using high resolution OCT, for example as taught herein above, an OCT probe may be used to perform an in-vivo biopsy. For example, locating the 3D position of nuclei of cells of tissue in-vivo may allow a clinician to determine if the nuclei locations are normal (for example in a lattice arrangement) or abnormal (for example in a chaotic arrangement). For example, chaotic arrangement of nuclei may be a sign of cancer whereas a lattice arrangement may be a sign of healthy tissue. For example, the some embodiments of the current invention may be used for an in-vivo prostrate biopsy.

It is expected that during the life of a patent maturing from this application many relevant technologies (for example diagnostic techniques and/or imaging techniques and/or optical scanning techniques) will be developed and the scope of the terms is intended to include all such new technologies a priori.

As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system comprising:
an adjustable frequency narrow band light source;
a beam splitter for dividing light from said light source along a sample and a reference path;
an adjustable frequency narrow band detector positioned to receive light from both the sample and the reference paths; and
a controller configured for:
controlling a frequency and bandwidth of said light source to emit light pulses over time in a succession of narrow frequency bands,
synchronizing said detector to said light source by tuning said detector to be sensitive to a respective narrow reception band that overlaps each narrow band of said succession of narrow bands when said each narrow band reaches said detector, and analyzing the output from said detector to estimate a reflectance distribution along a depth profile of the sample.

2. The system of claim 1, wherein said adjustable frequency narrow band light source includes a vertical-cavity surface-emitting laser (VCSEL).

3. The system of claim 1, wherein said adjustable frequency narrow band light source emits a coherent light.

4. The system of claim 1, wherein said adjustable frequency narrow band detector includes:

a light deflector having a frequency dependent angle of deflection, said light deflector receiving an incident light beam and producing a deflected beam;

a sensor array including a plurality of sensors, each of said plurality of sensors positioned, to receive said deflected beam at a different respective deflection angle corresponding to a respective narrow frequency band; said each sensor incremented from a base state to an exposed state by exposure to said deflected light of said respective narrow frequency band;

said controller further configured for adjusting a frequency sensitivity of said detector to said narrow reception band by activating at least one target sensor of said plurality of sensors; said target sensor positioned to receive said deflected light corresponding to said narrow reception band; said controller further configured for setting to said base state at least one other sensor while said target sensor is activated; said other sensor neighboring to said target sensor.

5. The system of claim 4, further comprising:

a plurality of reset circuits, each circuit of said plurality of reset circuits for setting at least one proper subset of said plurality of sensors to said base state, and wherein said each reset circuit is operationally controlled by said controller.

6. The system of claim 4, further comprising:

at least one reset circuit for setting at least some of said plurality of sensors to said base state, and at least one switch for connecting a proper subset of said plurality of sensors to said reset circuit wherein said at least one switch is operationally connected to and controlled by said controller.

7. The system of claim 5, wherein each circuit of said plurality of reset circuits connects said proper subset of said plurality of sensors to a ground.

8. The system of claim 1, wherein said light source is configured to emit a narrow band light having a bandwidth less than 1/10 the bandwidth of a full spectrum of said light source.

9. The OCT system of claim 1, wherein said detector is configured to have a narrow band sensitivity having a bandwidth less than 1/10 the bandwidth of a full spectrum sensitivity of said detector.

10. A method of comprising:

emitting light over a plurality of narrow illumination wave-bands, each narrow illumination wave-band emitted at a specified time and reaching a detector at a corresponding time;

dividing said light along a sample path and a reference path;

receiving light from both the sample and the reference paths at a detector;

synchronizing a frequency sensitivity band of said detector at said corresponding time to overlap said each illumination wave-band at said specified time and analyzing the output from said detector to derive a depth distribution of reflectance of a sample.

11. The method claim 10, wherein emitting is of a narrow band light having a bandwidth less than 1/10 the bandwidth of a full spectrum of said light source.

12. The method of claim 10, wherein said synchronizing includes configuring said detector with said sensitivity band having a bandwidth less than 1/10 the bandwidth of a full spectrum sensitivity of said detector.

13. The method of claim 10, wherein said synchronizing includes configuring said detector with said sensitivity band having a bandwidth less than 5 nm.

14. The method of claim 10, wherein said detector includes a sensor array, said sensor array including a plurality of sensors, the method further comprising:

deflecting said signal at a frequency dependent angle;

activating a first sensor of said plurality of sensors said first sensor positioned to be exposed to light deflected at an angle corresponding to said sensitivity band;

setting a second sensor to a base state while said first sensor is in said activated state.

15. The method of claim 14, wherein said setting includes connecting said second sensor to a reset circuit.

16. The method of claim 14, wherein said setting includes connecting said second sensor to a ground.

17. The method of claim 14, further comprising:

exciting said first sensor from said base state to an excited state according to a light intensity in said sensitivity band after said setting.

18. The method of claim 14, further comprising:

also exciting said second sensor from said base state to an excited state according to a light intensity in another frequency band after said setting.

19. The method of claim 18, further comprising:

resetting said first sensor to said base state simultaneous to said also exciting.

20. The method of claim 10, wherein said specified time and said corresponding time are substantially simultaneous.

* * * * *